(12) United States Patent
Van Herk et al.

(10) Patent No.: US 8,218,718 B1
(45) Date of Patent: Jul. 10, 2012

(54) RADIOTHERAPY AND IMAGING METHODS AND APPARATUS

(75) Inventors: Marcel Van Herk, Amsterdam (NL); Jan-Jakob Sonke, Amsterdam (NL)

(73) Assignee: Elekta AB (publ), Stockholm (SE)

( * ) Notice: Subject to any disclaimer, the term of this patent is extended or adjusted under 35 U.S.C. 154(b) by 0 days.

(21) Appl. No.: 13/150,534

(22) Filed: Jun. 1, 2011

(51) Int. Cl.
*A61B 6/00* (2006.01)
*A61N 5/10* (2006.01)

(52) U.S. Cl. .............................................. 378/7; 378/65
(58) Field of Classification Search ................. 378/7, 65
See application file for complete search history.

(56) References Cited

U.S. PATENT DOCUMENTS

| | | | |
|---|---|---|---|
| 4,998,268 A * | 3/1991 | Winter | 378/63 |
| 5,548,627 A * | 8/1996 | Swerdloff et al. | 378/4 |
| 5,651,043 A * | 7/1997 | Tsuyuki et al. | 378/65 |
| 6,219,403 B1 * | 4/2001 | Nishihara | 378/65 |
| 6,385,288 B1 * | 5/2002 | Kanematsu | 378/65 |
| 6,842,502 B2 * | 1/2005 | Jaffray et al. | 378/65 |
| 6,888,919 B2 * | 5/2005 | Graf | 378/65 |
| 7,227,925 B1 * | 6/2007 | Mansfield et al. | 378/65 |
| 7,263,164 B2 * | 8/2007 | Ghelmansarai et al. | 378/87 |
| 2006/0050847 A1 * | 3/2006 | Jaffray et al. | 378/65 |

* cited by examiner

*Primary Examiner* — Alexander H Taningco
(74) *Attorney, Agent, or Firm* — Sunstein Kann Murphy & Timbers LLP

(57) ABSTRACT

The present invention provides a method and an apparatus for reconstructing images from data acquired during radiotherapy. The approach is based on summing the imaging data acquired while both therapeutic and imaging source are active, with that acquired when only the therapeutic source is active. Further correction of the summed data can lead to reconstructed images of excellent quality.

13 Claims, 3 Drawing Sheets

RADIOTHERAPY AND IMAGING METHODS AND APPARATUS

FIELD OF THE INVENTION

The present invention relates to methods and apparatus for imaging a patient undergoing radiotherapy.

BACKGROUND ART

Radiotherapy techniques have improved dramatically in recent years. One particular improvement is the integration of radiotherapy with image acquisition devices such as cone-beam computed tomography (CBCT) scanners. In these systems, a moveable (e.g. rotatable) gantry supports a source of therapeutic radiation (i.e. in the megavolt range) as well as a source of imaging radiation (i.e. in the kilovolt range). A detector is positioned on the gantry substantially opposite the source of imaging radiation, and acquires imaging data as the gantry rotates around the patient. Such an imaging device allows efficient data collection for off-line decision protocols, validation of the patient geometry during actual therapy and detection of intra-fraction motion in two dimensions as well as cone-beam computed tomography (CBCT) to verify the patient anatomy in three dimensions.

Unfortunately, lateral scatter of the megavoltage (MV) beam into the kilovolt (kV) detector has a considerable impact on image quality. In general, the MV scatter depends on patient geometry, dose rate and field shape, and therefore it has been a prerequisite of conventional techniques to include values for these parameters in the CBCT reconstruction.

SUMMARY OF THE INVENTION

It is an object of the present invention to develop a MV-scatter correction scheme that does not require knowledge of values for these parameters.

One possible method for minimizing the impact of MV scatter would be to alternate therapeutic and imaging radiation sources; that is, to ensure that only the imaging source is active when the data is acquired from the detector. However, since one aims at minimal dose delivery times, interruption of the therapeutic radiation is not preferred.

Another possible approach is to pulse the therapeutic source of radiation on every frame, and the imaging source of radiation only on (say) even frames. Imaging data is acquired from the detector in each frame, such that successive images measure imaging data with therapeutic scatter, and therapeutic scatter only. In principle it is then trivial to subtract the MV scatter (odd frames) from the even frames to eliminate the MV scatter profile. The difficulty in this approach is that quantum noise in the scatter is doubled (it does not cancel) and that, due to the non-linear detector "ghosting" signal, significant artifacts occur in the final image.

In contrast, the present invention sums the data acquired in odd and even frames, as this leads to a clean image without artifacts (but with twice the scatter). The summed data can then be processed in order to estimate and remove the scatter from the therapeutic source of radiation.

In one embodiment, therefore, the present invention provides a method of imaging in an apparatus comprising a source of therapeutic radiation, a source of imaging radiation, and a detector of said imaging radiation, the method comprising the steps of: reconstructing images from first and second imaging data. The first imaging data was previously acquired during a first time frame in which both the therapeutic source and the imaging source are active. The second imaging data was previously acquired during a second time frame in which the therapeutic source is active and the imaging source is inactive. The reconstruction comprises at least the sub-steps of: summing said first and second imaging data to generate summed imaging data; and processing said summed imaging data to reconstruct an image.

It will be apparent to those skilled in the art that, in addition to a strict summation of the first and second imaging data, approximate sums will yield improved results over conventional approaches. For example, a sum of the first imaging data and 0.99 times the second imaging data will yield substantially the same results as if the first and second imaging data had been strictly summed; 99% of the artifacts may be corrected for. In the following, therefore, the terms "summed" and "added" (etc) are taken to include strict summation as well as summation of approximate or scaled values of one or both of the first and second imaging data (e.g. where one or both of the first and second imaging data are approximated, or multiplied by a factor $\alpha$, where $0<\alpha\leq 2$ in one embodiment, or $0.5\leq\alpha\leq 1.5$ in a further embodiment, or $0.8\leq\alpha\leq 1.2$ in a yet further embodiment).

BRIEF DESCRIPTION OF THE DRAWINGS

An embodiment of the present invention will now be described by way of example, with reference to the accompanying figures in which.

DETAILED DESCRIPTION OF THE EMBODIMENTS

The present inventors have developed a method and apparatus to correct for MV scatter reaching the kV detector during simultaneous acquisition of CBCT scans with rotational radiotherapy.

Figure 1:
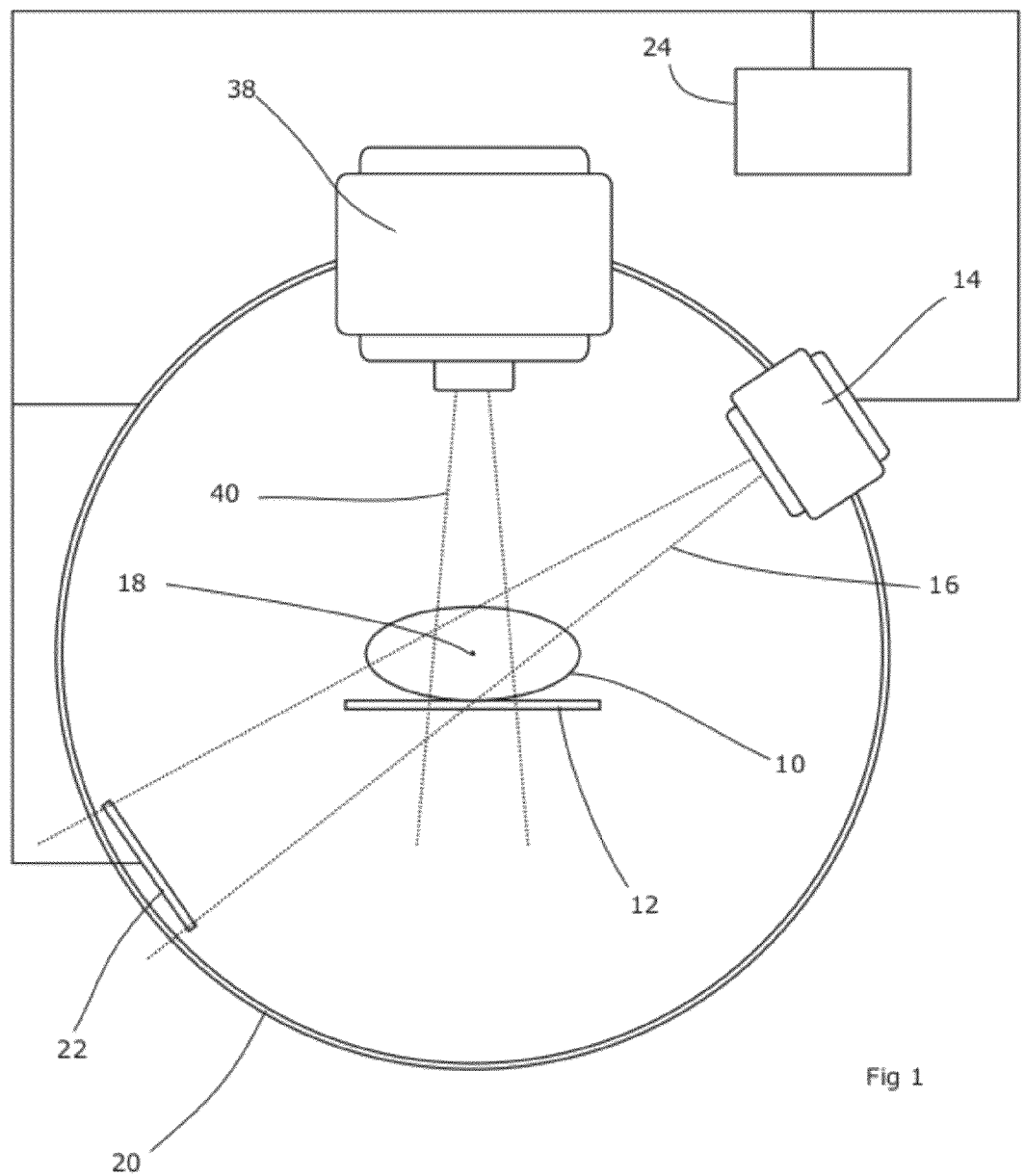
FIG. 1 shows an apparatus according to embodiments of the present invention.

FIG. 1 is a schematic diagram showing an apparatus according to embodiments of the present invention.

A patient 10 is supported on a couch 12 which may be of any suitable design. Couches typically allow the elevation, latitudinal and longitudinal position of the patient to be adjusted, and this may be provided for as desired. The couch 12 may also allow rotation in up to three rotational degrees of freedom (pitch, yaw and roll).

An x-ray source 14 is arranged to project a wide beam 16 of radiation generally directed towards the isocentre 18 of the system. The source 14 is rotatable around the isocentre 18 on a rotational support 20. The support can, for example, be in the form of a ring or annulus around the patient 10 and couch 12 in which the source is mounted, or it can be a C-arm, or any suitable support allowing the source to rotate or move, or any combination thereof. The radiation beam 16 will generally have an energy in the kV range, as that is most suitable for imaging purposes.

A two-dimensional flat-panel detector 22 is also mounted on the support 20, opposite the source 14 and arranged to rotate in synchronism therewith. If the support includes a C-arm then this can be achieved by mounting the detector on the opposite arm. Thus, radiation emitted by the source 14 is partially absorbed by the patient and the attenuated, scattered signal is detected by the flat panel detector 22.

The apparatus further comprises cables linking the source 14, detector 22 and rotational support 20 to processing means 24, which controls their respective operation, and processes the data generated including the images, source intensity (etc), and rotational support position. Data is output via any suitable means, e.g. a monitor but not limited thereto, and the system is controlled by any suitable input means, e.g. a keyboard but likewise not especially limited thereto.

The apparatus further comprises a source of therapeutic radiation 38 arranged to emit a suitably collimated beam of therapeutic radiation 40. Therapeutic radiation will typically have an energy in the megavolt range. Thus, imaging can take place during treatment.

As described above, a common problem in such systems is that a small proportion of the megavolt radiation from the therapeutic source 38 scatters from the patient and the surrounding apparatus into the detector 22. This high-energy radiation causes artifacts in the resulting images, obscuring the anatomical detail and degrading the image quality.

Embodiments of the present invention correct for these artifacts by controlling the therapeutic and imaging radiation sources according to a defined pattern: some imaging data is acquired with both the imaging 14 and therapeutic 38 sources active; some imaging data is acquired with just the therapeutic source 38 active. Processing circuitry 24 sums the data acquired in either case, as this leads to a clean image without artifacts (but with twice the scatter). The summed data can then be processed in order to estimate and remove the scatter from the therapeutic source of radiation.

Figure 2:
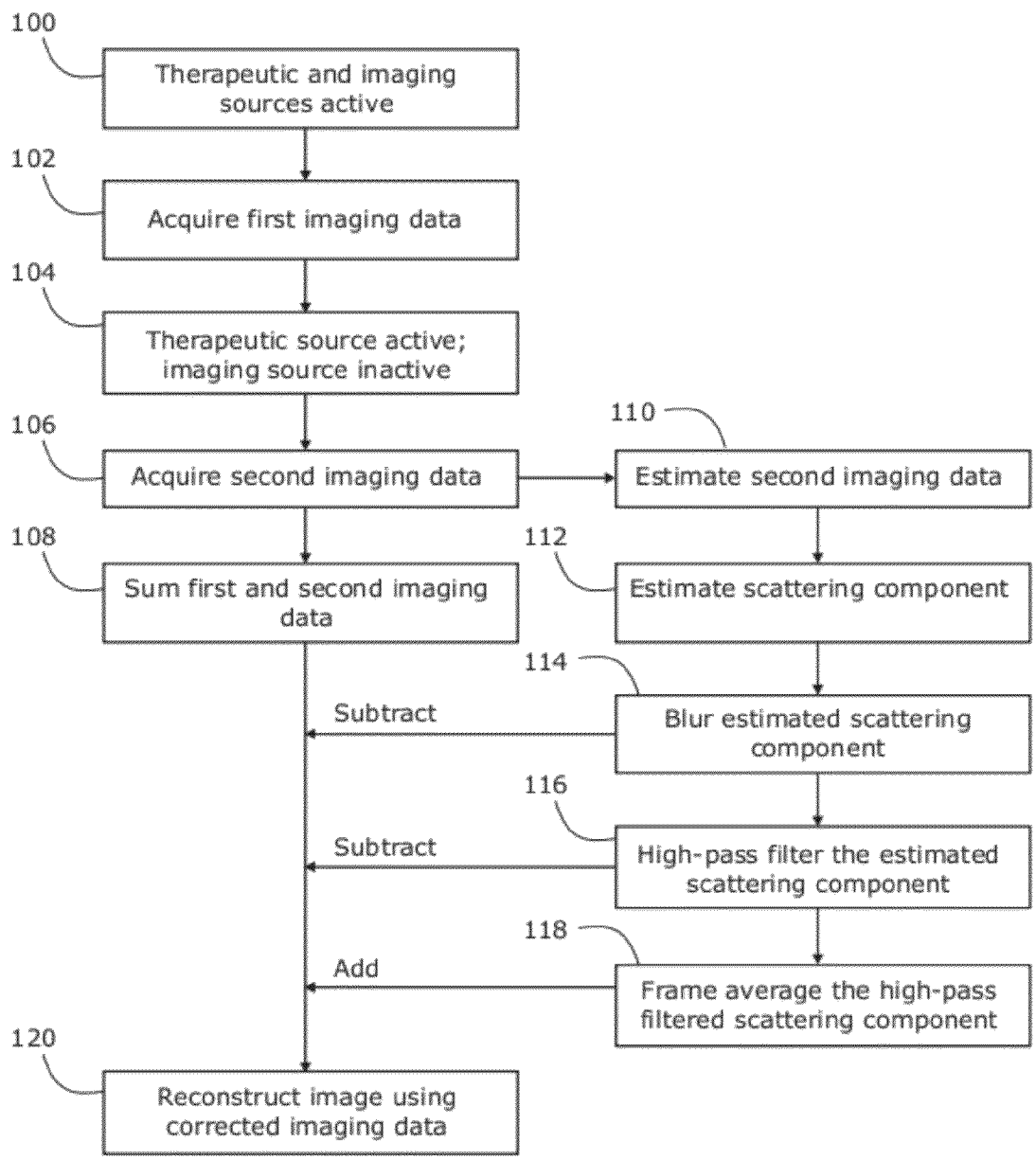
FIG. 2 is a flowchart of a method according to embodiments of the present invention.

The processing algorithm according to embodiments of the present invention is described below, to be read in conjunction with the flowchart in FIG. 2.

For ease of reference, the algorithm below employs a pulse pattern where time frames when both therapeutic and imaging sources are active (even frames) alternate with time frames when just the therapeutic source is active (odd frames). However, alternative pulsing patterns are equally possible.

Thus, in step 100, both the source of therapeutic radiation 38 and the source of imaging radiation 14 are active in a first time frame. In step 102, data is acquired from the detector 22 as a result of the accumulated radiation incident upon it in step 100.

In step 104, the therapeutic source 38 is active and the imaging source 14 is inactive during a second time frame. In an embodiment, the second time frame follows successively after the first time frame (for example, if the "therapeutic+imaging" time frames alternate with the "therapeutic" time frames); however, that need not be the case. The alternating pattern is one of many alternatives. Again, in step 106, data is acquired from the detector 22 as a result of the accumulated radiation incident upon it in step 104.

Mathematically, this situation is written as follows:

$I_0$=imaging data acquired while both therapeutic and imaging sources are active (even frames);

$I_1$=imaging data acquired while the therapeutic source is active and the imaging source is inactive (odd frames).

It has been found that the sum of $I_0$ and $I_1$ gives a clean image without artifacts, but with twice the scatter due to therapeutic radiation:

$$I_0 + I_1 = I + 2MV, \quad (1)$$

where I is the "ideal" image data, and MV is the scatter due to therapeutic radiation scatter in a single time frame (step 108).

To estimate the scatter MV, we first estimate $I_1$ from $I_0$, using gain images $G_0$ and $G_1$ $$\left(I_1 \approx \frac{G_1}{G_0} I_0\right).$$

See step 110. Gain images are acquired during calibration of the detector 22, to allow subsequently acquired imaging data to be normalized to account for variations in the sensitivity of each pixel in the detector. Gain image $G_0$ corresponds to a flood exposure of the detector as acquired during even time frames, and $G_1$ corresponds to a flood exposure of the detector as acquired during odd time frames. The difference between the estimate of $I_1$ and the measured value of $I_1$ is therefore:

$$I_1 - \frac{G_1}{G_0} I_0 = \left(1 - \left(\frac{G_1}{G_0}\right)\right) MV, \quad (2)$$

The value of $G_1/G_0$ will change from apparatus to apparatus. In the tested model, $G_1/G_0$ is approximately 0.05. It will be seen that equation (2) may be straightforwardly rearranged to provide an estimate of the MV scatter, MV (step 112).

However, this image contains noise and artifacts because $I_1/I_0$ is not equal to $G_1/G_0$ (due to non-linearities, etc). Therefore, in an embodiment of the present invention, the values of MV estimated according to equation (2) are blurred by applying a normalized low-pass filter (function LF) to estimate the MV scatter distribution (step 114). By rearranging equation (2) for MV, blurring the values to estimate the MV scatter distribution, and returning to equation (1), we find that:

$$I' = I_0 + I_1 - \frac{2}{\left(1 - \left(\frac{G_1}{G_0}\right)\right)} LF\left\{I_1 - \frac{G_1}{G_0} I_0\right\}, \quad (3)$$

where I' is an improved estimate of the image I without MV scatter.

However, I' still contains MV scatter noise from both $I_0$ and $I_1$ (also known as quantum noise). This noise has a relatively high spatial frequency, and can be separated from the MV scatter that has a low spatial frequency. The high-frequency quantum noise in I' is subtracted by applying a normalized high-frequency filter (function HF) to the estimate of MV obtained in equation (2) (step 116):

$$I'' = I' - \frac{1}{\left(1 - \left(\frac{G_1}{G_0}\right)\right)} HF\left\{I_1 - \frac{G_1}{G_0} I_0\right\}. \quad (4)$$

I'' is therefore a further improved estimate of the image I.

However, there are some high frequency components in the artifacts of I''. These are generally constant, and can be corrected by frame averaging the HF signal over a plurality of frames N (step 118) and adding this to the estimate I'':

$$\left\langle HF\left\{I_1 - \frac{G_1}{G_0} I_0\right\}\right\rangle = \langle HF \rangle, \quad (5)$$

-continued $$I''' = I'' - \frac{1}{\left(1 - \left|\frac{G_1}{G_0}\right|\right)} \langle HF \rangle,  \quad (6)$$

I''' is then a further improved estimate of the image data I, and can be fed to reconstruction code in the processing circuitry 24 so that an image can be produced (step 120). The average may be performed over all or selected frames acquired so far.

Figure 3:
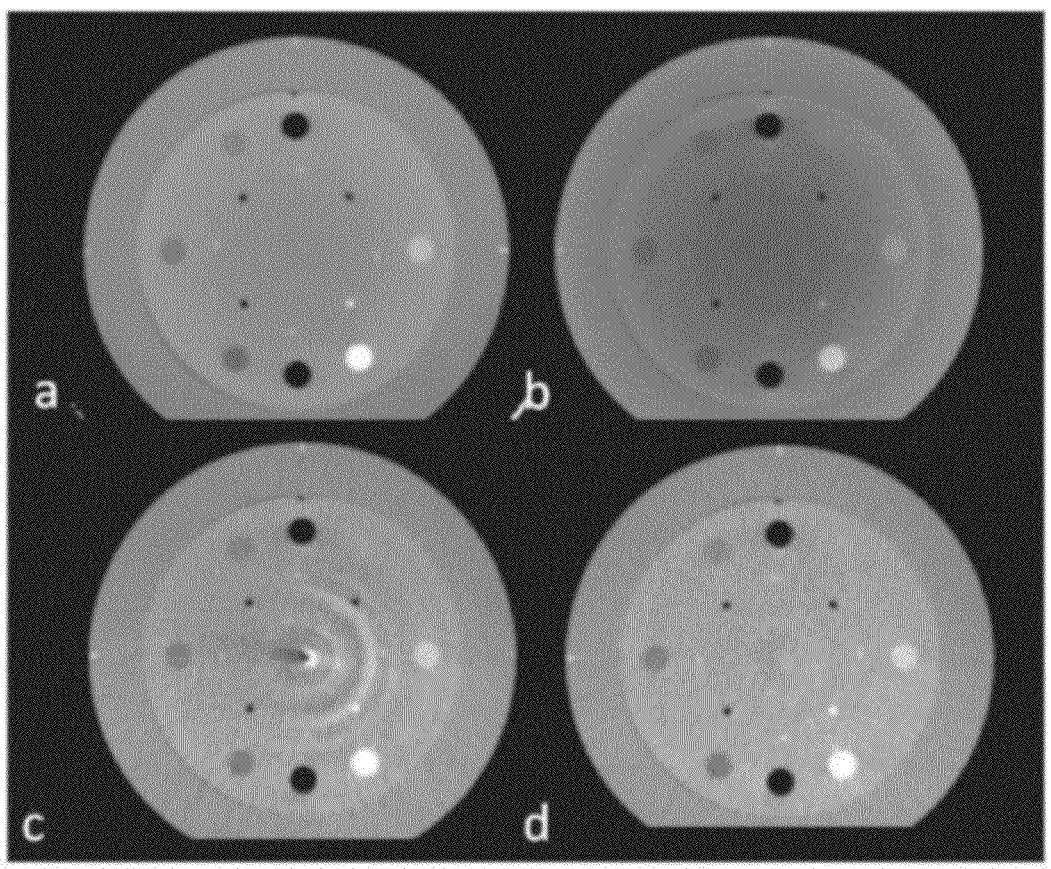
FIG. 3 shows images reconstructed according to various methods, including that of embodiments of the present invention in image d.

FIG. 3 shows imaging data acquired according to various methods, including that of embodiments of the present invention in image d. The method was tested on phantoms.

FIG. 3a shows a reconstructed image based on an apparatus without a therapeutic source active, i.e. "pure" CBCT. Without correction, acquisition during volumetric modulated arc therapy (VMAT) leads to significant cupping (FIG. 3b) owing to the MV scatter captured by the detector 22. Earlier in the application, a solution was described where the even frames are subtracted from the odd frames, $I=I_0-I_1$. The results of this approach are shown in FIG. 3c. Clearly, substantial artifacts are introduced due to non-linear ghosting.

FIG. 3d shows an image reconstructed on the basis of imaging data corrected according to embodiments of the present invention. The HF filter used in this example was a 3×3 unsharp mask filter, the LF filter dual application of a 41×41 pixel uniform smoothing filter.

It can be seen that image quality is significantly improved compared to the alternative dual therapy and imaging approaches in FIGS. 3b and 3c. Compared to acquisition without a therapeutic beam, the reconstruction quality is nearly identical. The reduced effective frame rate still allows a sufficient number of images to be collected as VMAT delivery times generally exceed CBCT scan times. Correction is performed in-line with acquisition, without introducing delays.

The present invention thus provides a method and an apparatus for reconstructing images from data acquired during radiotherapy. The inventive approach is based on summing the imaging data acquired while both therapeutic and imaging source are active, with that acquired when only the therapeutic source is active. Further correction of the summed data can lead to reconstructed images of excellent quality.

It will of course be understood that many variations may be made to the above-described embodiment without departing from the scope of the present invention.

The invention claimed is:

1. A method of imaging in an apparatus comprising a source of therapeutic radiation, a source of imaging radiation, and a detector arranged to detect said imaging radiation, the method comprising the steps of:
   reconstructing images from first and second imaging data, said first imaging having previously been acquired from said detector during a first time frame in which both the therapeutic source and the imaging source are active, said second imaging data having previously been acquired from said detector during a second time frame in which the therapeutic source is active and the imaging source is inactive;
   said reconstruction comprising at least the sub-steps of:
   i. summing said first and second imaging data to generate summed imaging data; and
   ii. processing said summed imaging data to reconstruct an image.

2. The method as claimed in claim 1, wherein said processing step comprises the sub-steps of:
   i. estimating a scatter component in each of the first and second imaging data as a result of the therapeutic radiation; and
   ii. subtracting said estimated scatter, or a multiple thereof, from said summed imaging data.

3. The method as claimed in claim 2, wherein said step of estimating the scatter component comprises the sub-steps of:
   i. estimating the second imaging data using the first imaging data and first and second gain images corresponding to the first and second time frames respectively; and
   ii. subtracting the estimated second imaging data from the acquired second imaging data to estimate said scattering component.

4. The method as claimed in claim 3, further comprising smoothing said estimated scattering component.

5. The method as claimed in claim 1, wherein the first and second time frames are successive.

6. An apparatus for treating a patient by radiotherapy, comprising:
   a source of therapeutic radiation;
   a source of imaging radiation;
   a detector arranged to detect said imaging radiation; and
   processing circuitry, configured to:
   acquire from said detector first imaging data during a first time frame in which both the therapeutic source and the imaging source are active;
   acquire from said detector second imaging data during a second time frame in which the therapeutic source is active and the imaging source is inactive; and
   reconstruct images from said first and second imaging data, said reconstruction comprising at least the sub-steps of:
   i. summing said first and second imaging data to generate summed imaging data; and
   ii. processing said summed imaging data to reconstruct a composite image.

7. The apparatus as claimed in claim 6, wherein the processing circuitry is further configured to, in said processing step:
   i. estimate a scatter component in each of the first and second imaging data as a result of the therapeutic radiation; and
   ii. subtract said estimated scatter, or a multiple thereof, from said summed imaging data.

8. The apparatus as claimed in claim 7, wherein the processing circuitry is further configured to, in said step of estimating the scatter component:
   i. estimate the second imaging data using the first imaging data and first and second gain images corresponding to the first and second time frames respectively; and
   ii. subtract the estimated second imaging data from the acquired second imaging data to estimate said scattering component.

9. The apparatus as claimed in claim 8, wherein the processing circuitry is further configured to smooth said estimated scattering component.

10. The apparatus as claimed in claim 6, wherein the source of therapeutic radiation, the source of imaging radiation and the detector are all mounted on a rotatable gantry.

11. The apparatus as claimed in claim 10, wherein the detector is mounted substantially opposite the source of imaging radiation.

12. The apparatus as claimed in claim 10, wherein the source of therapeutic radiation is mounted substantially orthogonal to the source of imaging radiation and the detector.

13. The apparatus as claimed in claim 10, further comprising a patient support for supporting a patient undergoing radiotherapy, a longitudinal axis of said patient support lying substantially parallel to an axis of rotation of said rotatable gantry.

\* \* \* \* \*